US00PP23332P2

(12) United States Plant Patent
Hammett

(10) Patent No.: US PP23,332 P2
(45) Date of Patent: Jan. 15, 2013

(54) ***DAHLIA* PLANT NAMED 'MYSTIC ENCHANTMENT'**

(50) Latin Name: *Dahlia variabilis*
Varietal Denomination: MYSTIC ENCHANTMENT

(76) Inventor: Keith Hammett, Auckland (NZ)

( * ) Notice: Subject to any disclaimer, the term of this patent is extended or adjusted under 35 U.S.C. 154(b) by 0 days.

(21) Appl. No.: 13/199,617

(22) Filed: Sep. 6, 2011

Related U.S. Application Data

(60) Provisional application No. 61/403,816, filed on Sep. 22, 2010.

(51) Int. Cl.
*A01H 5/00* (2006.01)

(52) U.S. Cl. ..... Plt./321

(58) Field of Classification Search ..... Plt./321
See application file for complete search history.

*Primary Examiner* — June Hwu
*Assistant Examiner* — Louanne Krawczewicz Myers

(57) ABSTRACT

A new cultivar of *Dahlia* plant named 'MYSTIC ENCHANTMENT' that is distinguishable by a compact rounded habit, glossy mahogany-black divided leaves and dark purple-brown stems. 'MYSTIC ENCHANTMENT' exhibits large bright red blossoms and dark central disks. In combination these traits set 'MYSTIC ENCHANTMENT' apart from all other existing varieties of *Dahlia* known to the inventor.

2 Drawing Sheets

Genus: *Dahlia.*
Species: *variabilis.*
Denomination: 'MYSTIC ENCHANTMENT'.

BACKGROUND OF THE INVENTION

The present invention relates to a new and distinct cultivar of *Dahlia* grown for use in mixed combinations, beds and the landscape. The new invention is known botanically as *Dahlia variabilis* and will be referred to hereinafter by the cultivar name 'MYSTIC ENCHANTMENT'. The specific epithet *variabilis* represents a hybrid seedling line that came from crossing various original wild species in the early 1800's, and refers to the species' wide range of flower color and shapes. *Dahlia* is in the family Compositae. The flower of 'MYSTIC ENCHANTMENT' is a "single" form blossom and exhibits a single row of ray florets surrounding a central cluster of disk florets.

'MYSTIC ENCHANTMENT' was selected as a seedling that resulted from the controlled cross-pollination carried out by the inventor in a cultivated area of Auckland, New Zealand. The breeding began in 1995 by crossing an individual plant *Dahlia variabilis* 'Colour Sucker' (unpatented) as the female parent and an individual of *Dahlia variabilis* 'Scarlet Fern' (U.S. Plant Pat. No. 18,989) as the male parent. Seed was collected from the female parent and coded as 7163/01, then sown with the intention of making a selection from the seedlings that resulted.

'MYSTIC ENCHANTMENT' was selected in 2005 based on the criteria of leaf color, leaf shape, plant height, self supporting plants, single blooms and flower color. Selection was conducted by the inventor, in Auckland, New Zealand. The unique traits that distinguish the new *Dahlia* variety named 'MYSTIC ENCHANTMENT' from other varieties of *Dahlia* known to the inventor are glossy mahogany-black divided leaves and profusions of bright red blooms with dark central discs. The new *Dahlia* named 'MYSTIC ENCHANTMENT' is distinguishable from the parents predominantly by flower and foliage color. The flowers of 'Scarlet Fern' are uniformly orange-red in color. The foliage of 'Colour Sucker' is less divided and lighter in color. The closest known variety of *Dahlia* known to the inventor is the inventor's variety and male parent, 'Scarlet Fern'. Whereas both 'Mystic Enchantment' and 'Scarlet Fern' bear mahogany-black divided leaves, the flowers of 'Scarlet Fern' are orange-red in color and the flowers of 'Mystic Enchantment' are saturated bright red in color. In addition, as a mature plant, 'Mystic Enchantment' is approximately 50% taller than 'Scarlet Fern'.

'MYSTIC ENCHANTMENT' exhibits a compact rounded habit, bright red flowers with dark central discs, glossy mahogany-black foliage, and dark purple-brown stems. The large single blossoms bloom in summer and fall. Cultural conditions include full sun, regular water and rich well-draining potting soil. 'MYSTIC ENCHANTMENT' is hardy to USDA Zone 9 and grows to 1.5 m in height and 1 m in width at maturity.

The first asexual reproduction of 'MYSTIC ENCHANTMENT' was conducted in 2005 in Auckland, New Zealand. The method of asexual propagation utilized was softwood cuttings from the tuber in year two and tissue culture thereafter. Since that time under careful observation, the distinguishing characteristics have been determined stable, uniform, and to be reproduced true to type in subsequent generations of asexual propagation.

SUMMARY OF THE INVENTION

The following traits have been repeatedly observed and represent the distinguishing characteristics of the new *Dahlia* cultivar named 'MYSTIC ENCHANTMENT'. These traits in combination distinguish 'MYSTIC ENCHANTMENT' from all other existing varieties of *Dahlia* known to the inventor. 'MYSTIC ENCHANTMENT' has not been tested under all possible conditions and phenotypic differences may be observed with variations in environmental, climatic, and cultural conditions, however, without any variance in genotype.

1. 'MYSTIC ENCHANTMENT' exhibits compact rounded habit.

2. 'MYSTIC ENCHANTMENT' exhibits glossy mahogany-black divided leaves and dark purple-brown stems.
3. 'MYSTIC ENCHANTMENT' is grown for use in mixed combinations, beds and the landscape.
4. 'MYSTIC ENCHANTMENT' exhibits large bright red blossoms and dark central discs.
5. 'MYSTIC ENCHANTMENT' blooms summer and fall.
6. 'MYSTIC ENCHANTMENT' grows to 1.5 m in height and 1 m in width at maturity
7. 'MYSTIC ENCHANTMENT' is hardy to USDA Zone 9.

BRIEF DESCRIPTION OF THE DRAWINGS

The accompanying color drawings labeled

The drawing labeled FIG. 1 depicts the entire plant in bloom and demonstrates that the foliage of 'MYSTIC ENCHANTMENT' is consistently mahogany-black when grown in full sun. Any part of the plant which is in shade, including the shade of other plant parts, turns to olive green in color. This coloration is reversible such that the olive-green foliage returns to mahogany-black when exposed or re-exposed to full sun.

The drawing labeled FIG. 2 depicts a close-up view of a flower.

Figure 1:
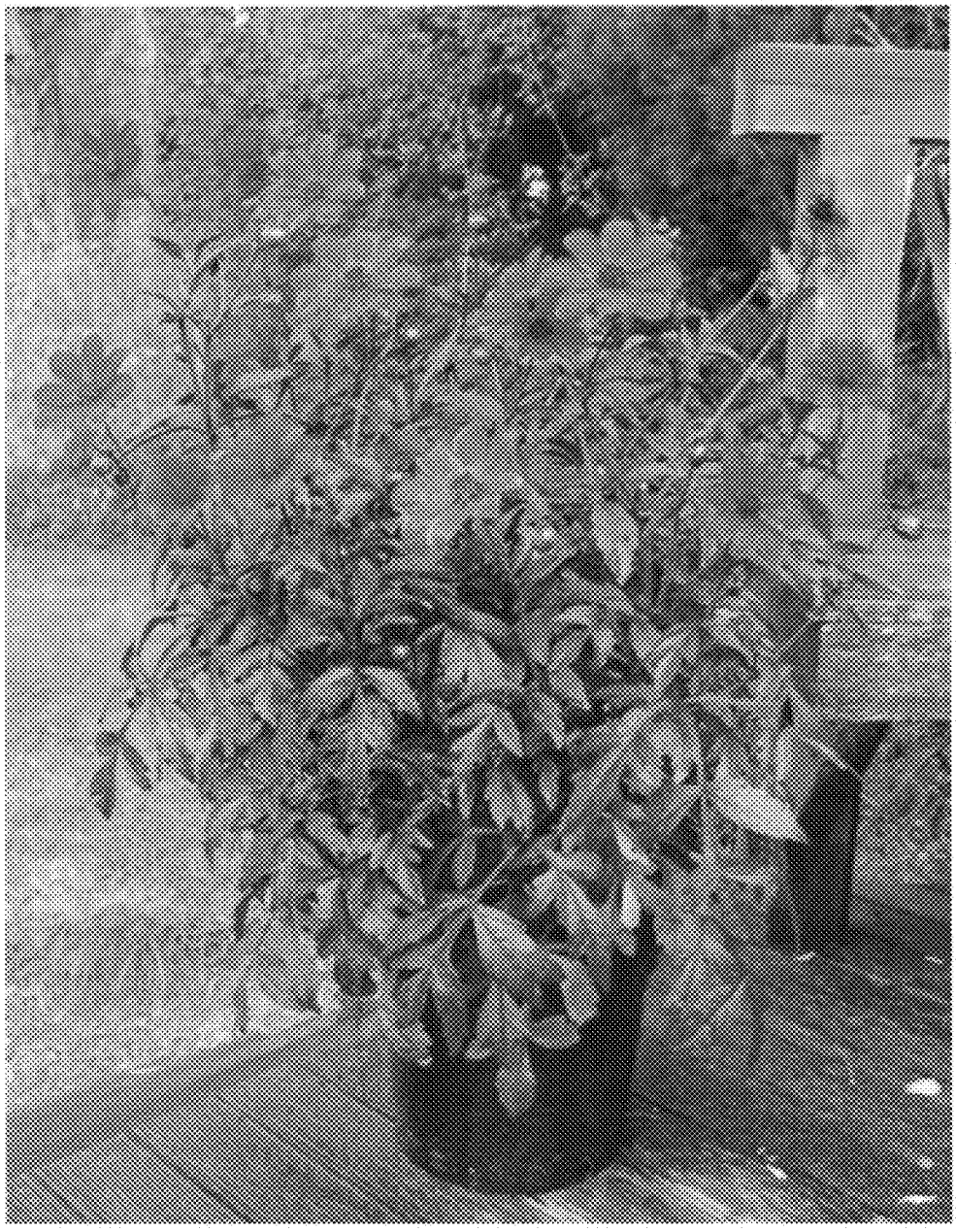
FIG. 1 and FIG. 2 illustrate the overall appearance of the new *Dahlia* cultivar named 'MYSTIC ENCHANTMENT' showing the colors as true as is reasonably possible to obtain in colored reproductions of this type. Colors in the photographs may differ from the color values cited in the detailed botanical description, which accurately describes the actual colors of the new *Dahlia* variety named 'MYSTIC ENCHANTMENT'.
Figure 2:
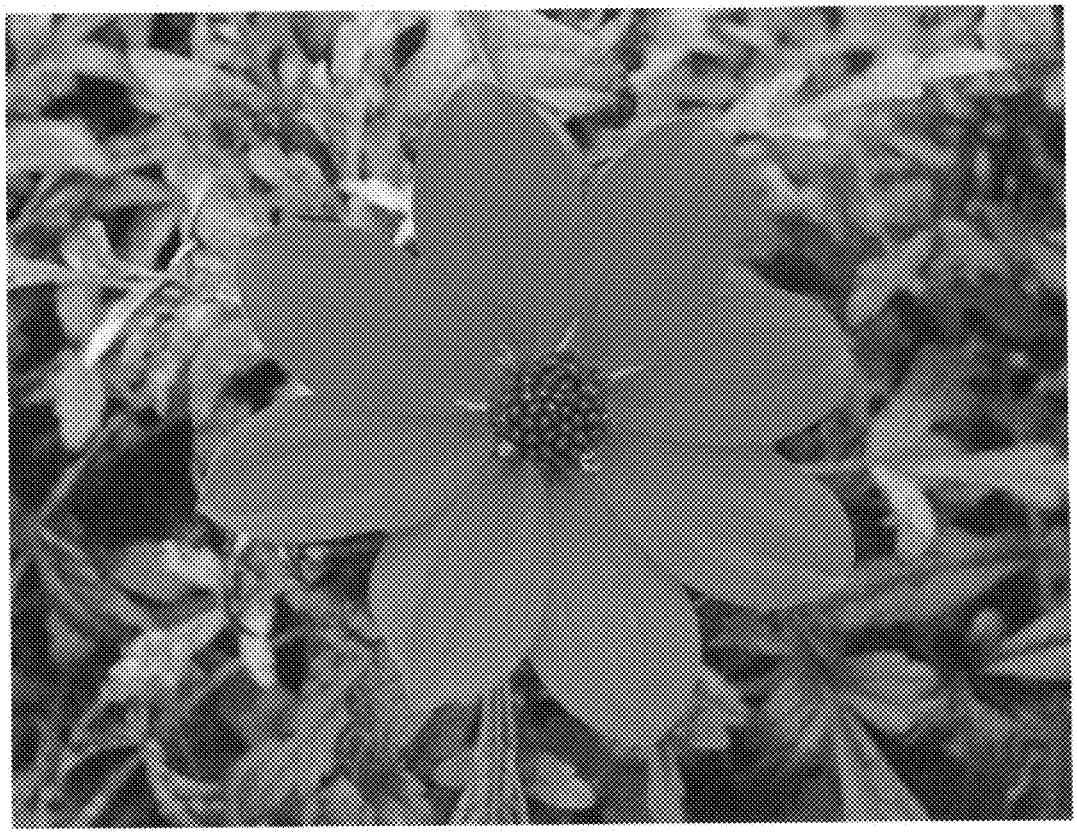

The drawings were made using conventional techniques and although flower and foliage color may appear different from actual color due to light reflectance, they are as accurate as possible by conventional photography.

BOTANICAL DESCRIPTION OF THE PLANT

The following is a detailed botanical description of the new *Dahlia* cultivar named 'MYSTIC ENCHANTMENT'. Observations, measurements, values and comparisons were collected in Santa Barbara, Calif. from a 12 month old plant grown in the landscape. Color determinations were made in accordance with The 2007 Royal Horticultural Society Colour Chart from London England, except where general color terms of ordinary dictionary significance are used. Growing requirements are similar to the species.

Botanical classification: *Dahlia variabilis* 'MYSTIC ENCHANTMENT'.
Family: Compositae.
Genus: *Dahlia.*
Species: *Variabilis.*
Denomination: 'MYSTIC ENCHANTMENT'.
Common name: *Dahlia.*
Parentage: *Dahlia variabilis* 'MYSTIC ENCHANTMENT' is a seedling that resulted from the controlled cross-pollination of the following parents:
- *Female parent.*—*Dahlia variabilis* 'Colour Sucker' (unpatented).
- *Male parent.*—*Dahlia variabilis* 'Scarlet Fern' (U.S. Plant Pat. No. 18,989).

Propagation method: Tissue culture and cuttings from virus-indexed mother stock.
Vigor: Vigorous.
Habit: Upright habit.
Use: For use in mixed combinations, beds and the landscape.
Type: Perennial.
Dimensions at 12 months of age from a cutting: 1.5 m in height, 1 m in width.
Cultural requirements: Grow in full sun with regular water, and well-draining potting soil.
Pest susceptibility: Susceptible to aphids.
Disease susceptibility: Susceptible to mildew in highly humid conditions.
Hardiness: USDA Zone 9.
Roots, tubers:
- *Rooting system.*—Fine and fibrous with stolons and tubers developing in long days.
- *Stolons.*—4 mm-55 mm in diameter, color 158C.
- *Tubers.*—Approximately 6 in number, ellipsoidal, dimensions varying from 3.5 cm in length and 2 cm in diameter to 7 cm in length and 3 cm in diameter.
- *Tuber surface.*—Smooth, color 158C with rough cuticle in places, color 199B.

Stem:
- *Color.*—N186C.
- *Shape.*—Cylindrical.
- *Dimensions.*—50 cm in length. Diameter ranges from 1.0 cm at base to 0.5 cm below uppermost leaf.
- *Surface.*—Glabrous.
- *Internode length* (*average*).—5 cm-12 cm.

Foliage:
- *Note on foliage color, applies throughout.*—The foliage of 'MYSTIC ENCHANTMENT' is consistently mahogany-black when grown in full sun. Any part of the plant which is in shade, including the shade of other plant parts, turns olive-green in color, typically in the range 147A to 152A. This coloration is reversible such that the olive-green foliage returns to mahogany-black when exposed or re-exposed to full sun. All the color readings in the botanical description are taken from foliage and leaf parts growing in full sun.

Type: Evergreen.
- *Leaf arrangement.*—Opposite.
- *Leaf division.*—Occasionally simple, predominantly compound as plant develops and matures. The compound leaf structure is very evident in a mature plant.

Simple leaves:
- *Leaf dimensions* (*average*).—10 cm in length and 8 cm in width.
- *Leaf shape.*—Hastate.
- *Leaf base.*—Attenuate.
- *Leaf apex.*—Apiculate.
- *Margin.*—Ciliate and pinnatisect.
- *Leaf color* (*adaxial surface*).—203A.
- *Leaf color* (*abaxial surface*).—147C.
- *Leaf venation pattern.*—Pinnate.
- *Veins.*—Adaxial surface: Visible only as depressions, color 203A. Abaxial surfaces: Prominent, raised, color N199A.
- *Leaf surfaces* (*abaxial surfaces*).—Slightly puberulent.
- *Leaf surfaces* (*adaxial surfaces*).—Glabrous.
- *Leaf attachment.*—Petiolate.
- *Leaf fragrance.*—None observed.
- *Petiole shape.*—Sulcate.
- *Petiole dimensions.*—0.5 cm to 2 cm in length and 3-4 mm in width.
- *Petiole color.*—Adaxial surface: 187B. Abaxial surfaces: 187B with streaks of 147C.

Compound leaves:
- *Division.*—Bipinnately compound consisting of two pairs of trilobed lateral leaflets and one trilobed terminal leaflet. Terminal lobe of terminal leaflet is joined (sessile) with the bases of the lateral leaflets.

*Compound leaf dimensions* (*average*).—24 cm in length and 22 cm in width.

*Leaflet dimensions*.—First pair (nearest stem) of lateral leaflets: Length 10.5 cm, width 6.5 cm. Second pair of lateral leaflets: Length 7 cm, width 3 cm. Terminal leaflet: Length 7 cm, width 3 cm.

*Leaflet attachment*.—First pair (nearest stem) of lateral leaflets: Petiolule. Second pair of lateral leaflets: Sessile to rachis. Terminal leaflet: Sessile to rachis.

*Leaflet shape, base, apex, margin, color, venation, surface are all identical for lateral leaflets and terminal leaflets as follows*.—Base: Attenuate. Apex: Apiculate. Margin: Ciliate and pinnatisect. Color (adaxial surface): 203A. Color (abaxial surface): 147C. Venation pattern: Pinnate. Veins: Adaxial surface: Visible only as depressions, color 203A. Abaxial surfaces: Prominent, raised, color N199A. Surfaces: Abaxial surfaces: Slightly puberulent. Adaxial surfaces: Glabrous.

*Compound leaf petiole* (*from stem to first pair of leaflets*).—Shape: Sulcate. Dimensions: 0.5 cm to 2 cm in length and 3-4 mm in width. Color: Adaxial surface: 187B, abaxial surfaces: 187B with streaks of 147C. Surfaces: Glabrous.

*Compound leaf radius* (*from first pair of leaflets to base of terminal leaflet*).—Shape: Sulcate with central midrib. Dimensions: 10 cm in length, 3 mm in width. Color: Adaxial surface: 187B, abaxial surfaces: 187B with streaks of 147C. Surfaces: Glabrous.

*First pair of leaflet petiolules*.—Shape: Sulcate. Dimensions: 3 cm in length, 1.25 mm in width. Color: Adaxial surface: 187B, abaxial surfaces: 187B with streaks of 147C. Surfaces: Glabrous. Stipules: Occasionally present singly or in pairs at axils of first and second pairs of leaflets. Attachment, sessile; division, simple; shape, elliptic with central vein, surface, smooth with entire margin; color 203A.

Inflorescence:

*Inflorescence type*.—Terminal: Flowers classified as "single" form, with single row of ray florets surrounding a central cluster of disk florets.

*Aspect*.—Facing upward and outward.

*Inflorescence quantity*.—15-20 per 2-litre container plant.

*Dimensions of inflorescence* (*average*).—8.5 cm in diameter and 2.0 cm in depth.

*Inflorescence shape*.—Radiate with center disk.

*Blooming seasons*.—Summer and fall.

*Fragrance*.—Slight fragrance when approached closely.

*Lastingness of flowers*.—Individual flowers remain intact on the plant outdoors for 7-10 days. Newly-opened flowers on cut flower stems remain intact in water indoors for 2 weeks.

*Peduncle*.—Dimensions (average): 20 cm in length and 0.3-0.4 cm in diameter. Shape: Cylindrical. Surface: Glabrous. Color: N186C.

*Bud*.—Shape: Oblate. Dimensions (average): 1.2 cm in height and 1.5 cm in diameter. Surface: Glabrous. Appearance: Semi-glossy. Color: 153D except 187B at flattened apex immediately prior to opening. Apex: Obtuse. Base: Truncate.

*Ray florets*.—Quantity per inflorescence: 8-10. Dimensions (average): 3.80 cm in length and 2.5 cm in width. Shape: Obovate. Apex: Obtuse with minute acute tip. Base: Cuneate. Margin: Entire. Surface (adaxial and abaxial): Glabrous. Arrangement: Radiate. Color (adaxial): 44B. Color (abaxial): N30A. Vein color (adaxial): Not evident: As leaf surface, barely visible. Vein color (abaxial): Parallel veins faintly visible, ranges between 159D and N155D.

*Disk florets*.—Quantity of disk florets: 50-60 per receptacle. Disk floret: Shape, tubular; corolla fused, dimensions: 1.3 cm in length and 1.5 cm in width. Disk floret color: 46A becoming burnt in appearance at apex, N77A. Disk floret apex: Acute. Disk floret surface (ventral and dorsal surfaces): Glabrous. Receptacle (disk) dimensions: 0.7 cm in depth and 2.5 cm in diameter. Receptacle surface: Glabrous. Receptacle color: 53A.

*Phyllary*.—Inner phyllary: Number: 8-10. Shape: Elongated ovate. Dimensions: 2.0 cm in length and 8 mm in width. Color (adaxial and abaxial surfaces): 151B except 139A at base. Texture: Scarious, waxy. Appearance: Translucent. Apex: Rounded to subacute. Base: Truncate. Margin: Entire. Surface (adaxial and abaxial): Glabrous. Outer phyllary: Number: 5 in number. Shape: Obovate. Dimensions: 1.0 cm in length and 0.6 cm in width. Color (adaxial surfaces): 200A. Color (abaxial surfaces): 147A, margins 200A. Form: Reflexed. Apex: Obtuse. Base: Truncate. Margin: Entire. Surface (adaxial): Glabrous, glossy, ribbed. Approximately 8 longitudinal ribs 0.5-0.8 mm apart. Surface (abaxial): Glabrous, glossy, smooth.

*Self-cleaning or persistent*.—Self-cleaning.

Reproductive organs:

*Androecium*.—(Present on disk florets only).

*Stamens*.—5 in number.

*Stamen attachment*.—Filament adnate to ventral surface of corolla.

*Stamen length*.—8 mm in length.

*Stamen color*.—150B.

*Anther*.—Connate.

*Anther color*.—25A.

*Pollen*.—Present.

*Quantity*.—Large amount.

*Pollen color*.—24A.

*Gynoecium*.—(Present on both ray and disk florets).

*Pistil*.—One present.

*Pistil length*.—15 mm in length.

*Stigma dimensions*.—3 mm in length and 0.5 mm in width.

*Stigma form*.—Plumose.

*Stigma color*.—N25A.

*Stigma shape*.—Bifurcate.

*Ovary position*.—Inferior.

*Ovary color*.—N144A.

*Ovary shape*.—Rotund.

*Ovary dimensions*.—2 mm in width and 3 mm in height.

Seed: None observed to date.

The invention claimed is:

1. A new and distinct cultivar of *Dahlia* plant named 'MYSTIC ENCHANTMENT' as described and illustrated herein.

* * * * *